United States Patent [19]

Erikson

[11] 4,281,550
[45] Aug. 4, 1981

[54] CURVED ARRAY OF SEQUENCED ULTRASOUND TRANSDUCERS

[75] Inventor: Kenneth R. Erikson, South Laguna, Calif.

[73] Assignee: North American Philips Corporation, New York, N.Y.

[21] Appl. No.: 104,528

[22] Filed: Dec. 17, 1979

[51] Int. Cl.³ ............................................. G01N 29/00
[52] U.S. Cl. ..................................... 73/626; 73/642; 128/660
[58] Field of Search ................. 73/626, 625, 628, 641, 73/642; 128/660; 367/105, 103, 117, 119, 122; 310/335, 336

[56] References Cited

U.S. PATENT DOCUMENTS

| | | | |
|---|---|---|---|
| 3,013,170 | 12/1961 | Sheldon | 73/618 |
| 3,881,466 | 5/1975 | Wilcox | 73/626 |
| 3,971,962 | 7/1976 | Green | 310/335 |
| 4,180,791 | 12/1979 | Tiemann | 73/626 |
| 4,183,249 | 1/1980 | Anderson | 73/642 |

*Primary Examiner*—Stephen A. Kreitman
*Attorney, Agent, or Firm*—Thomas A. Briody; Robert T. Mayer; Jack E. Haken

[57] ABSTRACT

An array of ultrasound transducers for pulsed sector-scan operation includes a plurality of transducer elements disposed on an arc of a circle and oriented to emit and receive ultrasound radiation in the direction of the center of the arc. A group of adjacent transducers within the array is active for each ultrasound pulse. The position of the group in the array is incrementally shifted along the arc, one transducer at a time, to effect scanning. The inherent focussing effect of a curved group of transducers is compensated with time delays or a negative lens to provide a parallel, sector-scanned radiation beam.

21 Claims, 9 Drawing Figures

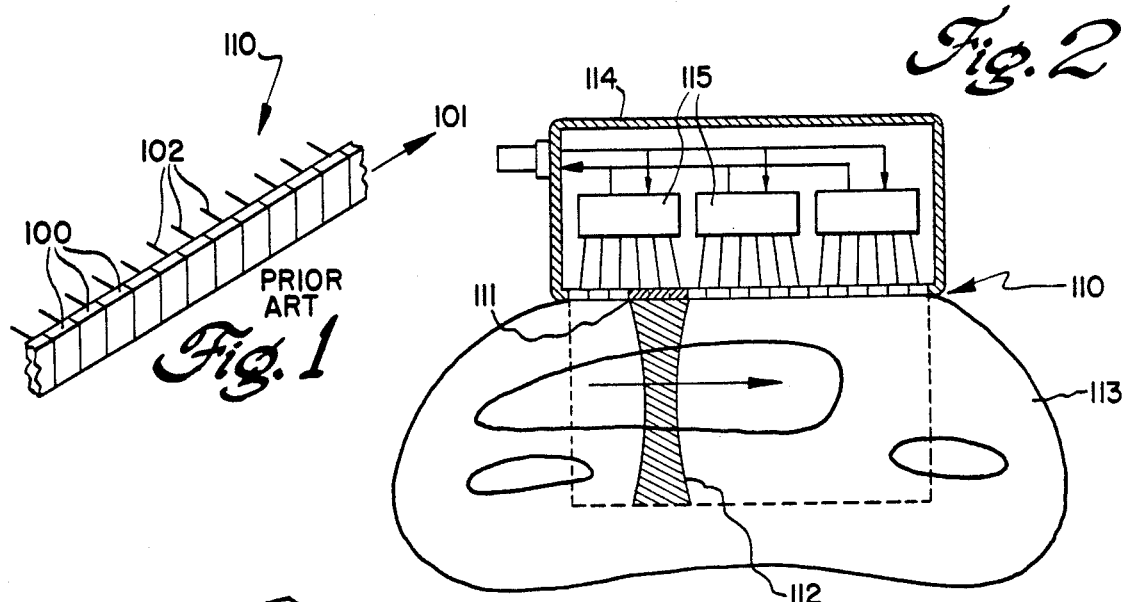
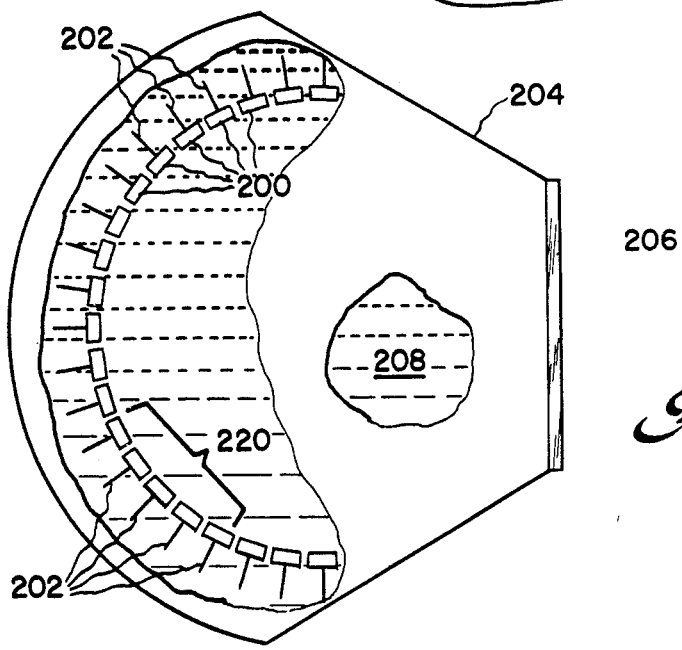
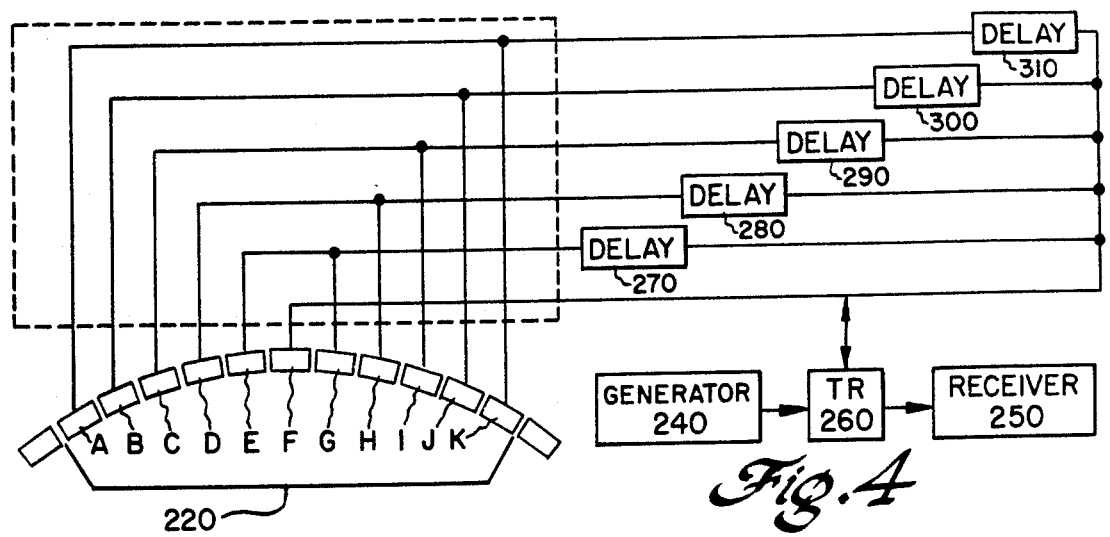

CURVED ARRAY OF SEQUENCED ULTRASOUND TRANSDUCERS

The invention relates to an array of ultrasound transducers which is particularly useful for medical imaging applications. More specifically, the invention relates to a curved, linear array of ultrasound transducer elements. A group of active elements are incrementally shifted along the array to sector-scan a parallel ultrasound beam.

BACKGROUND OF THE INVENTION

Internal body organs may be imaged and otherwise characterized by apparatus which directs pulses of ultrasound energy into the body and subsequently detects echoes which originate when the energy is reflected from tissue interfaces or other discontinuities within the body. In typical apparatus the ultrasound energy is directed into the body in a relatively narrow beam. Electric signals which describe the position and direction of the beam with respect to the body, as well as the relative arrival time and amplitude of the echos, are utilized to generate a visual display and/or mapping of the internal body structures. In many applications the direction of the ultrasound beam is manually controlled by a technician (generally by physical motion of a probe head) to build up a display pattern. While these methods are adequate for imaging stationary body structures, the time required for physical motion of a probe is generally much too long to image rapidly moving body structures (for example the valves in a beating heart) in real time. Ultrasound systems for generating real time displays of rapidly moving body organs generally utilize electromechanical or electronic means to change the position and direction of one or more beams of ultrasound energy with respect to the body.

Motion of a beam of ultrasound energy with respect to the body may be provided by sequentially activating transducer elements in a flat linear array to effectively scan an area of the body with a sequence of substantially parallel ultrasound beams. A device of this type is described in U.S. Pat. No. 3,013,170. A beam of ultrasound energy may, alternately, be scanned around a single origin point to produce a so-called "sector-scan." Sector-scan geometries are particularly useful since ultrasound energy may be directed between the ribs to scan the interior of the chest cavity. Sector-scanning has been achieved in the prior art by rapidly rotating one or more transducers about an axis, by steering energy from a fixed transducer with a rotating ultrasound reflector, or by sequencing individual transducer elements in a linear curved array. British Pat. No. 1,546,445 describes a curved transducer array with individual transducers which are individually activated to produce a sector-scan.

The transverse spatial resolution which may be obtained from a sequence array of ultrasound transducers is related to dimensions of the individual transducer elements in the array. Small transducer elements are desirable for obtaining fine resolution. The amount of ultrasound energy produced by an individual transducer element is, however, limited by its size. The signal-to-noise ratio of the returned ultrasound echoes necessarily depends on the amount of ultrasound energy introduced into the body. Thus, the signal to noise ratio suffers if small transducer elements are individually activated to achieve a scanning action. Diffraction effects will, furthermore, cause spreading of an ultrasound beam which originates from a single, small ultrasound transducer element.

This problem has been solved in the prior art by simultaneously activating a group of adjacent transducers within a flat linear array. Means were provided for incrementally shifting the active group along the array to provide fine spatial resolution and high signal-to-noise ratios. While this technique is appropriate for use with flat transducer arrays, which produce a parallel beam scanning geometry, the simultaneous activation of a group of adjacent transducers in a curved array inherently generates a focussed ultrasound beam. Sequenced group arrays have not, therefore, found application for the generation of high resolution sector-scans.

SUMMARY OF THE INVENTION

A concave linear array of small transducer elements is utilized to generate an ultrasound sector scan. A group of active elements is incrementally shifted along the array to provide a steerable beam providing high resolution and a high signal to noise ratio. Defocussing means, which compensate for the inherent focussing effects in a curved group of adjacent transducers, are provided. The defocussing means may comprise a negative ultrasound lens disposed between the array and the body. Alternately, the defocussing means may delay electrical signals, which are transmitted to and received from each transducer element in the active group, in proportion to the distance between that element and the center of the active group.

A curved array of small, high resolution transducer elements may be manufactured by first sawing the back surface of an electroded bar of piezoelectric ceramic to form a series of parallel grooves. A flexible matching window is cast on the front surface of the grooved bar. The bar and window are then bent around a convex mandrel so that the individual elements are fractured one from the other. A foam air cell is then cast over the back of the elements to retain them in place.

BRIEF DESCRIPTION OF THE DRAWINGS

The invention may be understood with reference to the attached drawings in which:

FIGS. 1 and 2 show a prior art sequenced flat array of ultrasound transducers;

FIG. 3 is a curved transducer array of the present invention;

FIG. 4 illustrates the principle of time delay defocussing for the array of FIG. 3;

DESCRIPTION OF THE PREFERRED EMBODIMENTS

Figure 5:
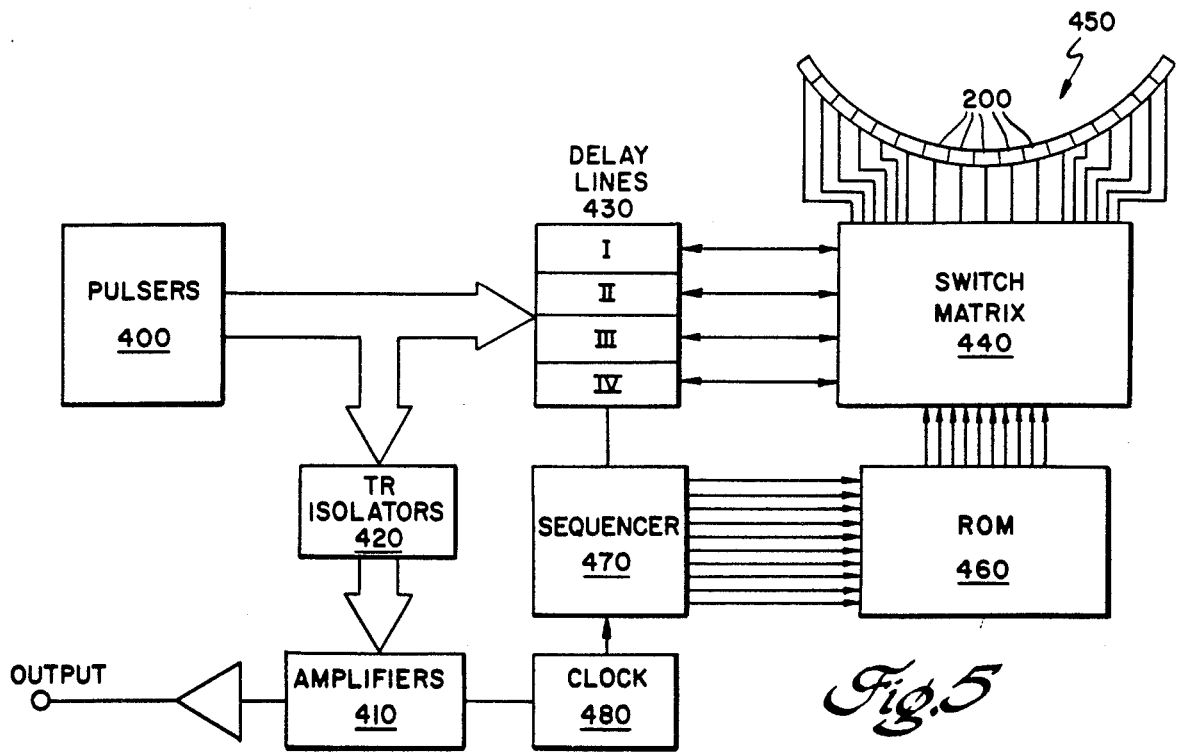
FIG. 5 schematically illustrates a system for operating the array of FIG. 3.

FIG. 1 is a linear array of ultrasound transducers 110 which is known in the prior art. A series of individual transducers elements 100 are disposed along a line 101. Separate electrodes 102 are provided for each transducer in the array and are connected to electronic circuits (not shown) which permit sequential activation of the elements to, in effect, move the source of an ultrasound beam along the line 101.

FIG. 2 illustrates an application of the array 110 of FIG. 1. A group of adjacent transducers 111 are simultaneously activated to produce a beam of ultrasound energy 112 which is inwardly projected into a body 113. The array 110 is disposed on the surface of a probe assembly 114 which includes switching circuits 115. The switching circuits act to incrementally shift the group of active transducers 111 along the array to generate a linear scan of the beam 112 with respect to the body. The operation of prior art imaging systems with incrementally shifted arrays is described in the articles *Ultrasonic Imaging Using Arrays*, Albert Macovski and *Methods and Terminology for Diagnostic Ultrasound Imaging Systems*, Maxwell G. Maginness in the Proceedings of the IEEE, Vol. 67, No. 4, April 1979 at page 484 and 641 respectively. Those articles are incorporated herein, by reference, as background material. As indicated in those articles, the incremental shifting of a group of transducers within the array improves spatial resolution and provides a higher signal to noise ratio than could be achieved by the sequential activation of individual transducer elements.

British patent specification No. 1,546,445 describes a curved linear array of transducers which are individually activated to generate a sector-scanned ultrasound beam. A positive (converging) lens is utilized with the transducer array to focus the beam through the spaces between the ribs. Because only one transducer element is active at a time, the array of British Pat. No. 1,546,445 suffers from relatively low spatial resolution and signal-to-noise ratio. The performance of the array cannot, however, be improved by directly applying the incrementally shifted active group geometry of FIG. 2 to the curved array configuration. The simultaneous activation of a group of adjacent elements on a curved array necessarily produces a sharply focussed beam which diverges in the far field and is unsuitable for medical imaging.

FIG. 3 schematically illustrates a transducer array of the present invention. A plurality of electro-acoustic transducer elements 200 are disposed along an arc and are oriented to project and receive ultrasound energy in the direction of the center of the arc. The individual elements 200 in the array are provided with separate electrodes and are connected, via wires 202, and a sequencing circuit to pulse generator and receiver circuits (not shown). The array is contained in a housing 204 which includes an ultrasound transmissive window 206. The housing may be filled with an ultrasound transmissive fluid 208, for example, castor oil, which is matched to the ultrasound transmissive properties of the human body. Alternately the housing may be filled with a solid material. In general the filling should have an acoustic attenuation between those of water and human tissue and should have an acoustic impedance which is matched to the impedance of human tissue.

A group of adjacent transducer elements (for example 220) within the array is activated for the transmission and reception of each ultrasound pulse. The active group of transducers is incrementally shifted along the array, one transducer at a time, on a pulse to pulse basis to provide a sector scan of ultrasound energy. Defocussing means are included to compensate for the strong inherent focussing of the curved array. The curved array, with an incrementally shifted group of active detectors, in combination with the defocussing means, produces a finer spatial resolution and higher signal to noise ratio than curved sequenced arrays of the prior art.

FIG. 4 illustrates a preferred embodiment of the defocussing means. At a given instant, a group 220 of adjacent transducers A-K within the array is activated by sequencing switches (not shown for the sake for clarity). The central transducer F within the zone is connected directly to ultrasound pulse generator 240 and receiver 250 circuits via a transmit-receive (TR) switch 260. The transducer pair E and G immediately adjacent the central transducer is connected to the TR switch 260 via a first delay 270. The next adjacent pair of transducers D and H are connected to the TR switch through a second delay circuit 280 which provides a longer delay than the delay circuit 270. Each next adjacent pair of transducers within the group (i.e. C and I, B and J, A and K) are connected to the TR switch via delay circuits (290, 300, 310) which provide increasing delays in proportion to the distance from the center of the active group to the associated transducers. The magnitude of the delays are chosen, using techniques which are well known in the art and which are described, for example, in the above referenced Macovski article, to compensate for the physical focussing effects of the curved array and thus provide a more parallel beam of ultrasound energy. Alternately the beam may thus be focussed at a point deep within the body of a patient.

FIG. 5 illustrates a system for incrementally shifting the active group along the transducer array. Pulsers 400, receiver amplifiers 410, and associated TR isolators 420 are connected in a conventional fashion to first ends of a bank of bidirectional delay lines 430. The bank of delay lines 430 includes delay lines of varying time delay which are calculated to provide the defocussing compensation for the active group as described above with respect to the FIG. 4. The opposite end of each delay line in the bank 430 is connected to a row of switches in an analog switch matrix 440. Each column of switches in the switch matrix 440 is connected to a separate element 200 in the transducer array 450. A separate switch (which may be a MOS transistor) is provided at each cross point (that is the intersection of each row with each column) in the switch matrix. The switching elements are individually activated by the output lines of a read-only memory (ROM) 460. Input lines of the read-only memory 460 are addressed by the output of a sequencer circuit which may be a sequential counter 470 driven by a clock 480. The sequencer circuit addresses consecutive words in the read-only memory which establish the connection patterns between the individual transducer elements in the array and corresponding delay lines to effect incremental shifting of a defocussed, active group along the array. As an example, Table I illustrates the first three words of a read-only memory which shifts an active group of nine transducer elements along an array by establishing connections to four delay lines I through IV.

TABLE I

| Delay Line | TRANSDUCER ELEMENT LOCATION | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | |
| I | 0 | 0 | 0 | 1 | 0 | 0 | 0 | 0 | 0 | 0 | 0 | 0 | 0 | |
| II | 0 | 0 | 1 | 0 | 1 | 0 | 0 | 0 | 0 | 0 | 0 | 0 | 0 | WORD 1 |
| III | 0 | 1 | 0 | 0 | 0 | 1 | 0 | 0 | 0 | 0 | 0 | 0 | 0 | |
| IV | 1 | 0 | 0 | 0 | 0 | 0 | 1 | 0 | 0 | 0 | 0 | 0 | 0 | |
| I | 0 | 0 | 0 | 0 | 1 | 0 | 0 | 0 | 0 | 0 | 0 | 0 | 0 | |
| II | 0 | 0 | 0 | 1 | 0 | 1 | 0 | 0 | 0 | 0 | 0 | 0 | 0 | WORD 2 |
| III | 0 | 0 | 1 | 0 | 0 | 0 | 1 | 0 | 0 | 0 | 0 | 0 | 0 | |
| IV | 0 | 1 | 0 | 0 | 0 | 0 | 0 | 1 | 0 | 0 | 0 | 0 | 0 | |
| I | 0 | 0 | 0 | 0 | 0 | 1 | 0 | 0 | 0 | 0 | 0 | 0 | 0 | |
| II | 0 | 0 | 0 | 0 | 1 | 0 | 1 | 0 | 0 | 0 | 0 | 0 | 0 | WORD 3 |
| III | 0 | 0 | 0 | 1 | 0 | 0 | 0 | 1 | 0 | 0 | 0 | 0 | 0 | |
| IV | 0 | 0 | 1 | 0 | 0 | 0 | 0 | 0 | 1 | 0 | 0 | 0 | 0 | |

The bit patterns of Table I are shortened for the sake of clarity of illustration; the principles illustrated therein may be extended to active groups and arrays which include larger or smaller numbers of transducer elements.

Figure 6:
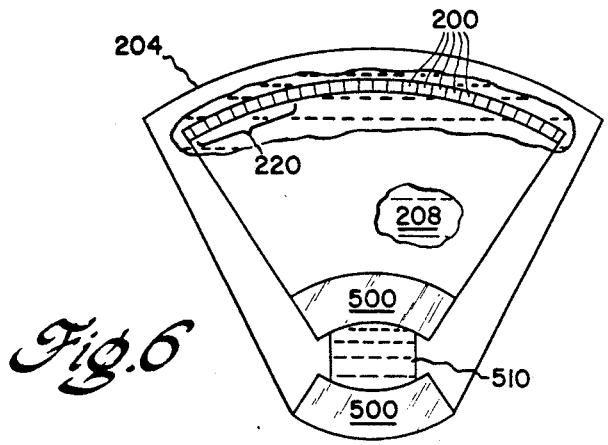
FIG. 6 is an alternate embodiment of the invention which includes a defocussing lens.

FIG. 6 is an alternate embodiment of a transducer array wherein the defocussing means comprise a negative lens 500. A group of transducers is sequentially shifted across the array as in the embodiment of FIG. 3 to produce a sector scan. All of the transducers in the group 200 may be simultaneously pulsed. Alternately, the delay line defocussing means of FIG. 4 may be utilized in conjunction with the lens 500. The lens may be constructed from metal or plastic and may advantageously comprise two negative lens elements separated by a fluid-filled cavity 510.

Figure 7:
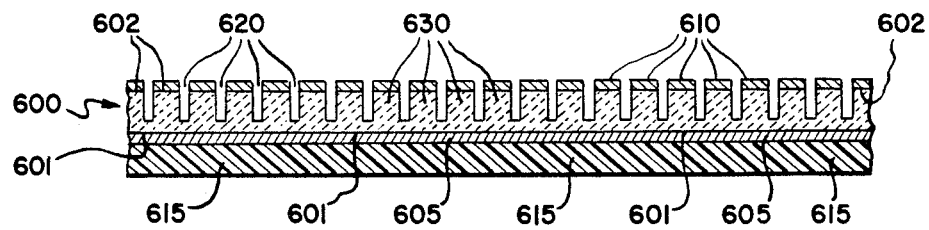
FIG. 7 illustrates a stage in the production of the array of FIG. 3.

FIG. 7 illustrates first steps in a perferred method for manufacturing the transducer array. The array is advantageously formed from a single rectangular bar 600 of piezoelectric ceramic (which may comprise Type PZT-5). Copper electrodes 605 and 610 are bonded to the front 601 and rear 602 major surfaces of the bar with a silver bearing epoxy resin. A flexible matching window 615 is then cast directly on the front electrode. The matching window may be advantageously cast from a mixture of two parts of a Stycast 1264 resin binder and one part tungsten powder. The window is cast by pouring the mixture directly onto the surface of the front electrode and allowing the tungsten powder to settle. After the resin is cured, the window is machined to a thickness of one quarter acoustic wavelength at the operating frequency of the array. For example, a window designed for operation at 3.5 MHz is machined to approximately 0.09 mm thickness.

A series of parallel grooves 620 are then cut through the rear electrode 610 and into the upper surface of the bar to segregate individual transducer elements 630 with their associated rear electrodes. Typically the grooves are approximately 0.13 mm wide and penetrate to 75% of the thickness of the ceramic bar.

In a preferred embodiment of the array the ceramic bar is approximately 80.5 millimeters long, 12.5 millimeters wide, and 2.0 millimeters thick. The bar is divided by 71 saw cuts to form 72 transducer elements. The rear electrodes on the endmost transducer elements are grounded to the front electrode so that the array comprises 70 functional transducer elements.

Figure 8:
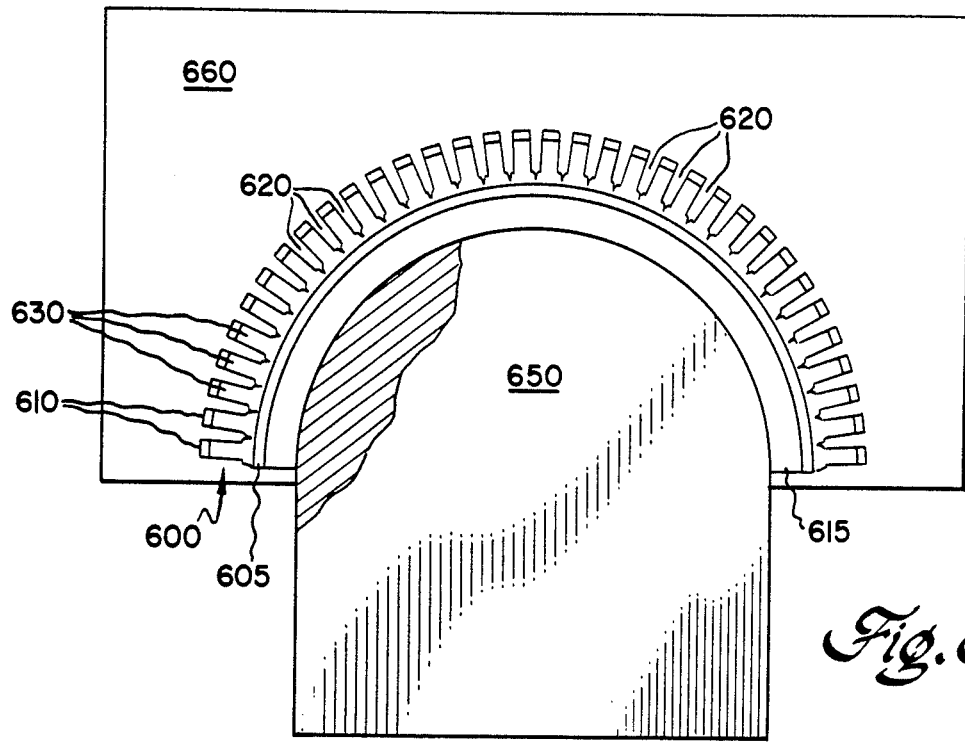
FIG. 8 illustrates a completed array.
Figure 9:
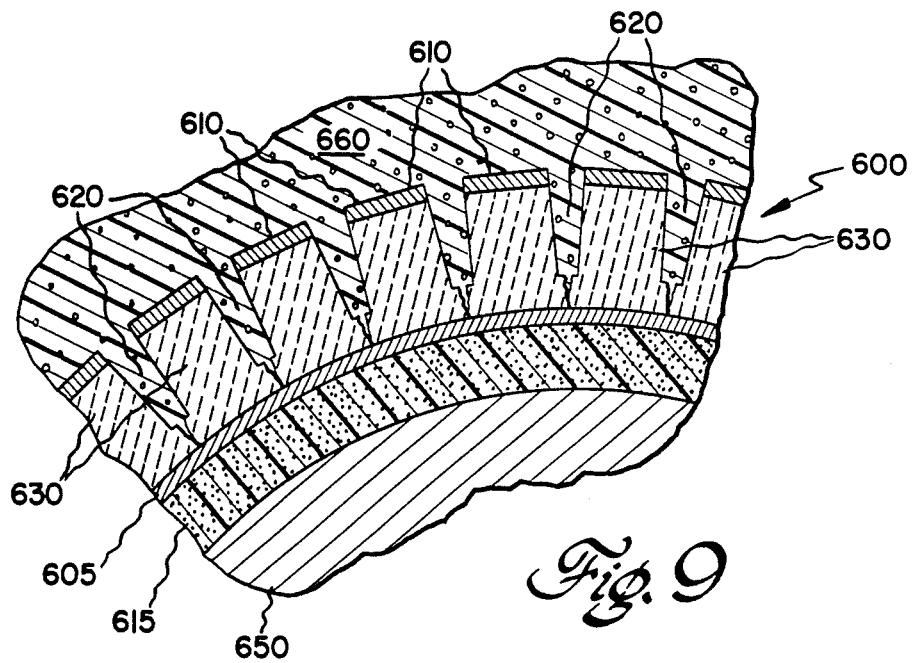
FIG. 9 is a detail of FIG. 8.

FIGS. 8 and 9 illustrate the further construction of the array. The grooved ceramic bar 600 with attached electrodes 605 and 610 and window 615 is formed around a semicylindrical mandrel 650, the grooves in the bar being parallel to the axis of the cylinder. As illustrated in detail FIG. 9 the bar cracks under each groove 620 to produce a curved array of separate, electroded transducer elements 630 which are retained in place by the front electrode 605 and window 615.

A supporting foam air cell 660 is then cast between the elements 630 and around the rear surface of the curved transducer array. The air cell retains the transducer elements in place and further provides a low acoustic impedance backing for the individual elements. The air cell may typically comprise glass micro-balloons in an epoxy resin binder.

In a preferred embodiment of the invention the upper electrodes 610 are wider than the ceramic bar and are folded back along the edges of the air cell to provide electrical connections to the individual elements.

What is claimed:

1. Apparatus for producing and/or receiving a sector scanned, substantially parallel beam of ultrasound energy comprising:
   an array, including a plurality of ultrasound transducer elements disposed along a curved line, each element being oriented to direct ultrasound energy toward and receive ultrasound energy from the center of the curve;
   means for transmitting electrical pulses to and receiving electrical pulses from the transducer elements;
   means for connecting a group of active transducer elements to the means for transmitting and receiving, the group of active elements comprising a preselected number of adjacent transducer elements in the array, said preselected number being greater than one and less than the total number of transducer elements in the array;
   means for sequentially changing the elements in the active group to incrementally shift the active group along the curve; and
   means for defocussing ultrasound energy produced and received by the transducer elements in the active group which means function to direct said energy between the active zone and a substantially parallel beam.

2. The apparatus of claim 1 wherein the means for defocussing comprise means for delaying the electrical pulses which are transmitted to and received from elements in the active group, pulses from each element being delayed in proportion to the distance between that element and the center of the active group.

3. The apparatus of claim 2 wherein the means for delaying comprise a plurality of electrical delay lines.

4. The apparatus of claims 2 or 3 wherein the means for delaying pulses are connected between the means for transmitting and receiving pulses and the means for connecting an active group.

5. The apparatus of claim 4 wherein the means for connecting an active group comprises a matrix of switches.

6. The apparatus of claim 5 wherein the means for sequentially changing comprises a read only memory having outputs connected to activate the switches and a sequencer circuit connected to sequentially address the read-only memory.

7. The apparatus of claim 1 wherein the means for defocussing comprise a negative lens disposed in the path of ultrasound energy projected from the elements of the active group.

8. The apparatus of claim 7 wherein the negative lens comprises materials selected from the group consisting of metals and plastics.

9. The apparatus of any of the claims 1, 2, or 7 wherein the transducer elements comprise a piezoelectric ceramic.

10. The apparatus of claim 9 wherein the elements comprises a PZT-5 ceramic.

11. The apparatus of claims 1, 2 or 7 wherein each element includes a front face directed toward the center of the curve and a back face directed away from the center of the curve and further comprising front and back conductive electrodes disposed, respectively, on the front and back faces of the elements.

12. The apparatus of claim 11 wherein a single continuous electrode is disposed across the front faces of all elements in the array.

13. The apparatus of claim 11 further comprising a matching window disposed adjacent the front surface of the transducer elements, the front electrode being disposed between the matching window and the transducer elements.

14. The apparatus of claim 13 wherein the matching window is one-quarter wave length thick at the operating frequency of the transducer array.

15. The apparatus of claim 13 wherein the matching window comprises tungsten powder in a resin binder.

16. The apparatus of claim 11 further comprising an air cell disposed over the rear electrodes of the transducer elements.

17. The apparatus of claim 16 wherein the air cell comprises glass micro-balloons in a resin binder.

18. The apparatus of any of claims 1, 2, or 7 wherein the array comprises approximately seventy active elements.

19. The apparatus of claims 1, 2 or 7 further comprising a fluid-tight housing surrounding said array and a fluid disposed within the housing.

20. The apparatus of claim 19 wherein the fluid comprises castor oil.

21. The apparatus of any of claims 1, 2, 3, or 7 wherein the means for transmitting and receiving comprise:
- a pulse generator having an output connected to drive all elements in the active zone;
- an ultrasound receiver having an input connected to sum pulses from all elements in the active zone; and
- a T-R switch connected to isolate the output of the pulse generator from the input of the receiver.

* * * * *